United States Patent [19]

Nappier

[11] Patent Number: 5,149,854

[45] Date of Patent: Sep. 22, 1992

[54] PREPARATION OF PLATINUM GROUP METAL AND RHENIUM CARBOXYLATES

[75] Inventor: Thomas E. Nappier, Parma, Ohio

[73] Assignee: Mooney Chemicals, Inc., Cleveland, Ohio

[21] Appl. No.: 624,648

[22] Filed: Dec. 10, 1990

[51] Int. Cl.$^5$ ............................................. C07F 15/00
[52] U.S. Cl. ..................................... 556/49; 556/136
[58] Field of Search ................................. 556/49, 136

[56] References Cited

U.S. PATENT DOCUMENTS

| | | | |
|---|---|---|---|
| 2,087,999 | 7/1937 | Salzburg | 260/11 |
| 2,252,662 | 8/1941 | Reiff | 260/429 |
| 2,252,665 | 8/1941 | Reiff | 260/429 |
| 3,562,181 | 2/1971 | Linn et al. | 252/430 |
| 3,646,079 | 2/1972 | Lawrenson et al. | 260/429 J |
| 3,652,613 | 3/1972 | Wright | 260/429 |
| 3,748,332 | 7/1973 | Wilkinson | 260/270 |
| 3,759,839 | 9/1973 | Fernholz et al. | 252/431 C |
| 3,960,909 | 6/1976 | Kunstle et al. | 260/429 J |
| 4,093,559 | 6/1978 | Fernholz et al. | 252/443 |
| 4,990,639 | 2/1991 | Bexten et al. | 556/136 |

FOREIGN PATENT DOCUMENTS

| | | | |
|---|---|---|---|
| 380213 | 8/1990 | European Pat. Off. | |
| 1214552 | 12/1970 | United Kingdom | 556/136 |
| 1301739 | 1/1973 | United Kingdom | 556/136 |

OTHER PUBLICATIONS

T. A. Stephenson et al.; "Carboxylates of Palladium, Platinum, and Rhodium and their Adducts," *J. Chem. Soc.*, 1965, 3632.

Abstract of Sharma et al., "Preparation of bisoxime palladium dichlorides, etc", *Kogyo Kagaku Zasshi*, vol. 72(7), pp. 1549–1551.

G. M. Vest et al., Final Report for Dec. 1, 1983–May 31, 1985, entitled "MOD Silver Metallization for Photovoltaics," pp. 14–19, 24–31, 49–51, 68–78, and 84–104.

PCT/US91/08802 Search Report filed Nov. 22, 1991.

*Primary Examiner*—Jose G. Dees
*Assistant Examiner*—Porfirio Nazario
*Attorney, Agent, or Firm*—Renner, Otto, Boisselle & Sklar

[57] ABSTRACT

The present invention relates to a process for preparing platinum group metal and rhenium salts of organic carboxylic acids and products obtained using the disclosed process. The process comprises reacting an alkali or alkaline earth metal salt of an organic carboxylic acid with a platinum group metal or rhenium salt in an organic liquid which at least partially dissolves the alkali and/or alkaline earth metal salt, the platinum group metal or rhenium salt, and the desired platinum group metal or rhenium carboxylate product, but is not a solvent for the salt formed between the alkali or alkaline earth metal and the anion of the platinum group metal or rhenium salt.

67 Claims, No Drawings

PREPARATION OF PLATINUM GROUP METAL AND RHENIUM CARBOXYLATES

TECHNICAL FIELD OF THE INVENTION

The present invention relates to methods for preparing platinum group metal and rhenium salts of organic carboxylic acids, to the solutions containing platinum group metal and rhenium salts thus obtained, and to metal-containing products prepared from such solutions.

BACKGROUND OF THE INVENTION

Many types and mixtures of metal salts and soaps of natural or synthetic organic acids, particularly carboxylic acids, have been suggested and commercially offered over several decades. These have been used to supply metals in forms which are soluble in organic liquids, particularly in various hydrocarbon oils and solvents, to form solutions having various desired properties and uses. For example, such metal salts have found uses as catalysts and as fuel and lubricant additives. Metal salts of carboxylic acids also are useful as stabilizers for various polymers including polyvinyl chloride-type plastics, and in the area of drying catalysts for paints, varnishes and other coating compositions.

The metal salts of carboxylic acids which have been suggested in the prior art include salts formed with a variety of metals including noble and precious metals such as silver, gold, platinum, palladium, osmium, rhodium, iridium, ruthenium, etc. Platinum, its oxides and salts, including organic as well as inorganic salts, have been widely used as catalysts in fuel cells, for abatement of noxious emissions from automobile and industrial exhaust gases, in hydrogenation reactions and in catalytic oxidation reactions such as for preparation of acetic acid, nitric acid from ammonia, etc. Additionally, solutions containing precious metal salts in solvents such as hydrocarbon solvents are particularly desirable. It also is desirable that the solutions of precious metal catalysts be of high purity and essentially free of negative ions which may inhibit certain catalytic reactions.

Stephenson et al, "Carboxylates of Palladium, Platinum and Rhodium, and their adducts," Journal of The Chemical Society (1965) pp. 3632-3640, describes obtaining diacetoplatinum (II) by careful reduction with formic acid of solutions of hexahydroxyplatinate (IV) in acetic acid and preparations of certain rhodium carboxylates are also described. The preparation of diacetoplatinum (II), however, is difficult due to the risk of explosion inherent in the preparation of this compound. This risk has been reported by J. E. Kinsella in CHEM. & IND., pp. 550 (1970) and by E. W. Malerbi, CHEM. & IND., pp. 796 (1970) using a different method. Malerbi also reports that a method to overcome the risk of explosion by Davidson and Triggs reported in the Kinsella, supra, has disadvantages such as that the product is usually contaminated with platinum and the yield tends to be low and variable.

Takiguchi et al, "Synthesis of naphthenates of gold, silver, platinum and palladium and bisoxime palladium dichlorides," Kagyo Kagaku Zasshi, Vol. 72, No.7, (Japan 1969) pp. 1549-1551, describes reactions of chloroauric acid and chloroplatinic acid with sodium naphthenate, reporting that the direct reaction between an aqueous solution of chloroauric acid and sodium naphthenate lacked reproducibility and yield and the direct reactions between chloroplatinic acid and sodium naphthenate caused marked precipitation of metal and "did not produce a good result."

U.S. Pat. No. 3,652,613, issued on Mar. 28, 1972, describes a process for the production of a platinous carboxylate containing two or more carbon atoms by reacting at an elevated temperature a platinic halide with a carboxylate containing two or more carbon atoms of a metal which forms a halide insoluble in the reaction medium. Saturated ethers, carboxylic acids, esters, and ketones are mentioned as suitable inert liquid media. Column 2, lines 1-2, refer to silver carboxylates as "preferred" metal carboxylates.

U.S. Pat. No. 3,700,458 (Lindholm) describes a chemical process for preparing noble metal salts of carboxylic acids useful in photosensitive and thermosensitive compositions. The process involves mixing a non-aqueous solution of an organic carboxylic acid with a non-aqueous solution of a noble metal trifluoroacetate or tetrafluoroborate in the presence of an organic peptizer. A variety of organic peptizers are disclosed including polyvinyl acetals and certain acrylate copolymers.

Vest et al, "Final Technical Report: MOD Silver Metallization for Photovotaics," Department of Energy DOE/JBL/956679--84, Distribution Cat. UC-63 (Purdue Research Foundation, Jul. 1, 1985) pp. 1-52, describes preparation of platinum (II) 2,4-pentanedionate and platinum (II) 2-ethylhexanoate at pages 17 and 18. The preparation of 2,4-pentanedionate is reported as carried out by dissolving potassium tetrachloroplatinate (II) in 8 mL of hot water and stirring in potassium hydroxide dissolved in 2 mL of water. The solution is warmed until it becomes yellow at which time acetyl acetone is added. The report states that when this mixture is heated to 50° C. with frequent shaking, a pale yellow precipitate of platinum 2,4-pentanedionate is gradually formed over a period of 1 to 1.5 hours. The preparation of the 2-ethylhexanoate is reported as prepared by stirring a solution of potassium tetrachloroplatinate into an equal molar mixture of 2-ethylhexanoic acid and triethylamine. The resulting solution is stirred at room temperature for one hour and then heated to 50° C. in a water bath and stirred at that temperature for 2 to 3 hours. The report then states that a black oil separates from this solution which is removed, washed with cold water and then warm water (50°-60° C.) until no chloride ions were detected in the wash water with silver nitrate. The black oil is then extracted in about 40 mL of benzene and dried over a molecular sieve.

Similarly, Vest and Singaram, "Material Research Society Symposium Proceedings", vol. 60, pg. 35 (1986) describes a production of ruthenium 2-ethylhexanoate from ruthenium trichloride trihydrate and triethyl ammonium 2-ethylhexanoate in 68% yield.

SUMMARY OF THE INVENTION

The present invention relates to a process for preparing platinum group metal (hereinafter "PGM") and rhenium salts of organic carboxylic acids and the PGM and rhenium carboxylate products thus obtained. The process comprises reacting an alkali or alkaline earth metal salt of an organic carboxylic acid with a PGM or rhenium salt in an organic liquid at a temperature sufficient to form the desired organic PGM or rhenium carboxylate. The PGMs include platinum, palladium, osmium, ruthenium, iridium and rhodium. Preferred organic liquids are ones which are solvents for the alkali or alkaline earth metal carboxylate and the PGM or rhenium salt, but which are not solvents for a salt formed between the alkali or alkaline earth metal of the starting carboxylate and the anion of the PGM or rhenium salt. The process of the present invention results in the formation of the desired PGM and rhenium carboxylates which generally are characterized as high purity products. The products may be recovered as a filtrate and further purified by redissolving the product in a second organic liquid. The second organic liquid is preferably different from the organic liquid used during the above reaction procedure.

Solutions prepared from the resulting PGM and rhenium carboxylates have numerous uses. They are useful as homogeneous catalysts and they may serve as starting materials for making heterogeneous PGM and rhenium catalysts; printed circuits, resistive coatings, electrical contacts, solder contacts, and hybrid interconnects for electronic devices; sensor components such as oxygen sensors and temperature sensors; piezo-electric units; electrodes; reflective or semi-reflective coatings on glass; solar collector cells and cell coatings; antireflective coatings; decorative coatings; ceramic matrix composites; metal and metal oxide coated ceramics; pharmaceuticals relating to chemotherapy; etc.

DESCRIPTION OF THE PREFERRED EMBODIMENTS

The process for preparing the PGM and rhenium carboxylates in accordance with the present invention comprises, in one embodiment, the steps of (A) preparing a mixture of (1) at least one alkali or alkaline earth metal salt of an organic carboxylic acid, (2) at least one PGM or rhenium salt having an anion other than the carboxylate anion of (A)(1), and (3) an organic liquid capable of at least partly dissolving the at least one alkali or alkaline earth metal salt of an organic carboxylic acid of (1) and the at least one PGM or rhenium salt of (2), which is not a solvent for a salt formed between the alkali or alkaline earth metal of (1) and the anion of (2); and (B) maintaining the mixture (A) at a temperature below the decomposition temperature of components (A)(1), (A)(2) and (A)(3) and PGM or rhenium carboxylate product for a period of time sufficient to form the PGM or rhenium carboxylate.

The PGM and rhenium salts may be selected from any which have an anion capable of forming an alkali or alkaline earth metal salt of (A)(1) which is insoluble in the organic liquid. Examples include PGM and rhenium chlorides and bromides, such as platinum dichloride, platinum trichloride, platinum tetrachloride, platinum dibromide, chloroplatinic acid, palladium dichloride, palladium dibromide, ruthenium trichloride, osmium trichloride, rhenium pentachloride, rhenium tetrachloride; rhenium trichloride, rhenium oxychloride, iridium trichloride, rhodium trichloride, etc.; nitrates, such as rhodium trinitrate; and sulfates, such as rhodium sulfate. Platinum tetrachloride and dichloride are preferred among the platinum salts. These compounds are commercially available and/or may be prepared using well known preparation methods such as described in *Kirk-Othmer's Encyclopedia of Chemical Technology*, 3rd Edition, Volume 18, pages 254–259 (platinum), 261–263 (iridium), 263–265 (rhodium), 267–269 (ruthenium) and 270–277 (platinum group compounds in general) and Volume 20 of the same, pages 255–258 (rhenium), the text of which are hereby fully incorporated herein by reference with regard to such methods.

As noted, the preparation of the PGM and rhenium carboxylates by the process of the present invention is conducted in an organic liquid which can be any organic liquid in which the alkali or alkaline earth metal salts derived from the alkali or alkaline earth metal carboxylate and the PGM or rhenium salt are relatively insoluble. Examples of organic liquids which can be utilized in the process of the present invention include carboxylic acids or anhydrides such as acetic acid, propionic acid, butyric acid, 2-ethylhexanoic acid, decanoic acid, isooctonoic acid, isononanoic acid, neodecanoic acid, dodecanoic acid, etc.; esters and ester-acids of carboxylic acids or anhydrides such as methyl acetate, ethyl acetate, and diethyl acetate; ketones such as acetone and methyl ethyl ketone; hydroxy-containing organic compounds including saturated aliphatic alcohols such as methanol, ethanol, propanol, butanol and isobutanol, unsaturated aliphatic alcohols such as allyl alcohol, etc.; aromatic solvents including benzene, toluene, xylene, cumene, psuedo cumene and mesitylene; saturated ethers, e.g., saturated aliphatic ethers such as di-n-propyl ether or di-isopropyl ether or a cyclic ether such as tetrahydrofuran (THF) or dioxane; nitrile solvents such as acetonitrile; halocarbons such as methylene chloride or dichloroethane; etc. Among these, the carboxylic acids or anhydrides, ketones, saturated aliphatic alcohols, aromatic solvents, saturated aliphatic ethers, and cyclic ethers are preferred, and among these, acetone, methyl ethyl ketone, propanol, xylene and THF are preferred.

The alkali or alkaline earth metal salts of organic carboxylic acids from which the PGM and rhenium salts can be prepared include unsubstituted, substituted, or polyfunctional aliphatic, alicyclic and aromatic mono- and polybasic carboxylates. The organic carboxylates may be either natural or synthetic, or mixtures thereof. Functional moieties include ether, ester, thioester, ketone, amine, nitrile and heterocyclic linking groups and substituents. Examples of alkali or alkaline earth metal salts of natural acids, although usually refined, include alkali or alkaline earth metal salts of straight- and branched-chain carboxylic acids, including mixtures such as tall oil acids, and alkali or alkaline earth metal salts of cyclic carboxylic acids such as naphthenates. A variety of synthetic carboxylates, and particularly aliphatic carboxylates or mixtures thereof, are useful, and these generally will contain two or more carbon atoms in the carboxylate moiety. The aliphatic carboxylates used in the present invention can contain from 2 to about 30 carbon atoms, and the alicyclic carboxylates can contain from 5 to about 30 carbon atoms. Aromatic carboxylates contain from 7 to about 30 carbon atoms. The alkali metal carboxylates are generally preferred for the low solubility of the alkali metal halides in many organic liquids.

Generally, the aliphatic carboxylates will contain at least 4 carbon atoms, preferably at least about 6 carbon atoms, and more preferably at least about 8 carbon atoms and will generally contain up to about 18 carbon atoms, in some embodiments up to about 12 carbon atoms and in others up to about 10 carbon atoms. In one embodiment, at least about 80 weight-percent of the organic carboxylates are these preferred aliphatic carboxylates. When metal salts comprising more than one carboxylic acid are employed, the metal salts of carboxylic acids containing, for example, at least about six carbon atoms may be employed advantageously in combination with metal salts of carboxylic acids having as few as two carbon atoms as one of the acids of the metal salt mixture.

Examples of useful organic carboxylates include alkali and alkaline earth metal salts of acetic acid, propionic acid, butyric acid, isopentanoic acid, hexanoic acid, 2-ethylbutyric acid, benzoic acid, nonanoic acid, decanoic acid, 2-ethylhexanoic acid, isooctanoic acid, isononanoic acid, neodecanoic acid, dodecanoic acid, lauric acid, palmitic acid, stearic acid, oleic acid, linoleic acid, commercially available mixtures of two or more carboxylic acids such as naphthenic acids, tall oil acids, rosin acids, etc.

The alkali or alkaline earth metals of the carboxylate reactants may be any which form a carboxylate which is soluble in the organic liquid, but which form a relatively insoluble precipitate with the anion of the PGM or rhenium salt reactant in the same organic liquid. The expression "relatively insoluble precipitate" is defined herein to mean that the alkali or alkaline earth metal salt is sufficiently insoluble to drive the reaction in favor of PGM and rhenium carboxylate formation. Generally, the organic liquid is selected such that the solubility of the alkali or alkaline earth metal salt is not more than 1.0 gram per 100 grams of the organic liquid. Preferably, the solubility of the alkali or alkaline earth metal salt is not more than about 0.001 gram per 100 grams of organic liquid, and more preferably is not more than about 0.0001 gram per 100 grams of organic liquid. Published solubility data, such as the solubility data compiled in Linke, *Solubilities: Inorganic and Metallo-Organic Compounds*, 4th ed. (Amer. Chem. Soc'y. 1965) may be utilized to select appropriate cations, anions and organic liquid combinations. This reference is hereby fully incorporated herein by reference as it relates to such solubility data. Examples of insoluble alkali metal salt/organic liquid combinations include sodium and potassium chlorides in organic liquids such as the acid corresponding to the carboxylate moiety, another carboxylic acid, acetone, propanol, tetrahydrofuran, etc.

The reaction between the PGM or rhenium salt and the organic carboxylate can generally be carried out at temperatures of from about 0° C. to about 150° C. for a period of time sufficient to form the desired PGM or rhenium salt as long as condition (B) above is met. More often, the reaction temperature will be at least about 20° C. and often at least about 45° C. Generally, the reaction temperature will be not more than about 100° C. and often is not more than about 80° C. A temperature of about 56° C. is preferred when acetone is the organic liquid, since that is the reflux temperature of acetone at atmospheric pressure. Generally, the reaction will be completed within about 24 hours, and often will be substantially complete within about 6 hours of when it is initiated. Reaction times within about 4 hours can be used to achieve a PGM or rhenium carboxylate product yield of at least 80 wt. % in most cases. Yields as high as 90 wt. % or higher can often be achieved. The period of time required for reacting the PGM or rhenium salt with any particular carboxylate in solution can be readily determined by one skilled in the art.

After the reaction is completed, the organic liquid generally is filtered to remove any undesirable solids which may be present. The filtrate is a solution containing the desired PGM or rhenium salt. Depending on the amount of organic liquid used in the reaction, the filtrate may be concentrated under vacuum to provide solutions having higher concentrations of the PGM or rhenium salt.

In another embodiment of the present invention, the PGM or rhenium carboxylate is prepared by the above-described steps (A), and (B), and optional steps of (C) filtering the product of (B) and recovering the filtrate and (D) evaporating the organic liquid of (A)(3) from the filtrate and redissolving the filtrate in a second organic liquid different from the organic liquid of (A)(3).

In a preferred embodiment, steps (A), (B), (C) and (D) are followed by the further steps of (E) filtering the solvent containing the dissolved filtrate residue.

Steps (C) and (D), and optionally (E), further refine the product obtained in steps (A) and (B) by utilizing an organic liquid which is a good solvent for the PGM and rhenium carboxylate in step (D) relative to contaminants such as the alkali and alkaline earth metal salts produced as a byproduct. In one embodiment of the present invention, the organic liquid of (A)(3) is a ketone and the second organic liquid of (D) is an aromatic solvent. The steps in one preferred embodiment utilize acetone as the organic liquid in (A)(3) and xylene as the second organic liquid in (D).

Contrary to the requirements of (A)(3), the second organic liquid of (D) is not necessarily a solvent for the reactants of (A), namely the alkali or alkaline earth metal carboxylate and the PGM or rhenium salt, unless it is desirable to provide conditions for continued reaction between the reactants as in steps (A) and (B).

In yet another embodiment of the present invention an organic liquid may be used in the reaction step that has a sufficiently high boiling point that it would be difficult to remove the organic liquid from the PGM or rhenium carboxylate by heating and reducing pressure without decomposing the PGM or rhenium carboxylate. In that case, it may be desirable to conduct the reaction in a minimum amount of the high boiling solvent and then rinse the reaction vessel, precipitates, and filter medium with a volatile PGM or rhenium carboxylate solvent into the filtrate solution. Heat and/or reduced pressure can then be used to remove the volatile solvent without decomposing the PGM or rhenium carboxylate. One example of such a protocol would be to conduct the reaction in 2-ethylhexanoic acid and rinse the reaction vessel, precipitates and filter medium with pentane, collecting the wash, and evaporating the pentane to concentrate the PGM or rhenium carboxylate in the filtrate.

The amount of alkali or alkaline earth metal salt of an organic carboxylic acid added to the mixture in step (A) is not critical. Similarly, the concentration of the PGM and rhenium salts in the mixture prepared in step (A) is not critical and may be varied over a wide range. Generally, the concentration of the PGM and rhenium salts will be from about 1 to about 40% by weight, preferably from about 10 to about 20% by weight. Typically, the reactants are mixed in about stoichiometric amounts, but in some instances, an excess of a reactant may be used to force the reaction to completion. Generally, the molar ratio of alkali or alkaline earth metal carboxylate to PGM and rhenium salts is in the range from about 1:1 to about 10:1.

The amount of organic liquid added to the mixture in step (A) should be an amount which will yield a solution of the desired PGM and rhenium carboxylate in acceptable concentration. Generally, the solutions of the PGM and rhenium salts of organic carboxylic acids obtained in accordance with the present invention preferably contain at least about 3 wt. %, and more preferably at least about 6 wt. %, PGM and rhenium. The concentration of PGM and/or rhenium can approach the theoretical limit that may be present in the formulae for the carboxylate salts sans solvent in which the number of equivalents of PGM and/or rhenium equals the number of equivalents of the carboxylate. Concentrations as high as about 50% or more by weight of PGM and rhenium can be obtained. Typically, the metal concentration is at least up to about 30% by weight. The organic phase containing organic liquid and PGM and rhenium carboxylate can be further diluted with solvent to provide solutions containing the desired concentration. The organic solvent can be evaporated from the PGM and rhenium carboxylate so that the PGM and rhenium carboxylate can be used neat or redissolved in a completely different solvent, such as in above-described optional step (D), when the organic liquid or solvent is sufficiently volatile. The solutions may be filtered to remove suspended particles.

The following examples illustrate the process of the present invention and PGM and rhenium carboxylate solutions which are prepared in accordance with the process of the invention. Unless otherwise indicated in the following examples and elsewhere in the specification and claims, all parts and percentages are by weight, all temperatures are in degrees Celsius, and all pressures are at or near atmospheric.

EXAMPLE 1

13.8 g of platinum tetrachloride and 21.5 g of sodium neodecanoate are warmed to 56° C. in 150 mL of acetone and are stirred for 3 hrs. The slurry is filtered and acetone is evaporated from the solution. The residue is dissolved in 100 mL of xylene and insoluble material is separated by centrifuging. The remaining solids are washed with additional xylene and xylene layers are combined. The product (131.6 g) contains 6.59% platinum (88% yield).

EXAMPLE 2

Following the same procedure as in Example 1 above, a mixture of 30.11 g of $PtCl_2$ and 15.92 g of $PtCl_4$ are reacted with 83 g of sodium neodecanoate in 500 mL of acetone. The slurry is stirred at 56° C. for 2 hrs and is filtered; then the acetone is distilled off in vacuo. The solid is dissolved in 200 mL of xylene and is filtered again. The product contains 8.74% Pt and weighs 327 g (93% yield).

EXAMPLE 3

34.96 g of $PtCl_4$ and 200 mL of acetone are mixed and 59 g of sodium benzoate is added. The slurry thickens so acetone is added to 800 mL and the slurry is heated to reflux temperature. The solids gradually dissolved to produce an orange-brown solution. After 4 hours the solids obtained by centrifuging a sample are white. The solution (354 g) obtained after filtering contains 6.5% Pt (96.8% yield).

COMPARATIVE EXAMPLE 1

A slurry of potassium hexachloroplatinate (65.2 g in 100 mL of water) is reduced to potassium tetrachloroplatinite by adding 6.13 g of 35% hydrazine in 100 mL of water dropwise while heating to 80° C. The solution is evaporated to dryness and partially dissolved in 100 mL of warm water (50° C.). A mixture of 98.2 g (0.55 mol) of neodecanoic acid, 52.5 g of triethylamine (0.52 mol), and 50 mL of water is added to the platinum solution and warmed to 50° C. After stirring the solution for 3 hours black solids begin to form; the solution is cooled and 1500 mL of water is added after 2.5 more hours. The black, oily layer which forms overnight is decanted away from the water and is washed with four 125 mL portions of water until no chloride ions are detected in the wash. The washed oily layer is dissolved in 200 mL of xylene, filtered and dried over molecular sieves. The product, 165 g, contains 3.35% Pt (21.6 wt. % yield).

COMPARATIVE EXAMPLE 2

A 40 g portion of a mixture of triethylamine (50.5 g, 0.50 mol), 2-ethylhexanoic acid (80.3 g, 0.55 mol), and water (50 mL) is stirred and warmed with 21.4 g of potassium tetrachloroplatinite in 50 mL of water. After one hour at 45°–50° C. a mirror and solids begin forming. The reaction is stopped by extracting the solution with two 100 mL portions of xylene. The mixture is centrifuged and the xylene layer is separated from the solids and water with each extraction. The first extraction is 99.6 g, 1.31% Pt, and the second is 99.4 g, 0.13% Pt. The two layers are combined and reduced in volume on a rotary evaporator to 33.8 g, 4.27% Pt (14.4 wt. % yield).

EXAMPLE 4

121.8 grams of $RuCl_3 \cdot 3H_2O$ is dissolved in 300 mL of ethanol and is stirred with 254 grams of sodium 2-ethylhexanoate and 15 grams of 2-ethylhexanoic acid. The mixture is warmed to 70° C. for 6 hours and then is filtered. The ethanol is removed by heating in vacuo. The thick bluish-black oil, 281 grams, contains 15.2% Ru (82.9% yield).

EXAMPLE 5

The procedure of Example 1 is followed, except the rhenium trichloride is substituted for platinum tetrachloride on an equal equivalents of metal basis, producing rhenium neodecanoate.

EXAMPLE 6

20 g of iridium chloride trihydrate is dissolved in 200 mL of ethanol and is stirred with 28.4 grams of sodium 2-ethylhexanoate and 4 g of 2-ethylhexanoic acid. The solution is stirred for 10 hours at ambient room temperature, warmed to 60° C. and filtered. The ethanol is removed by heating in vacuo. The thick yellowish-brown oil, 34.6 g, contains 25.4% Ir (82% yield).

EXAMPLE 7

80 g of rhodium trichloride trihydrate is dissolved in 600 mL of ethanol and is stirred with 158 grams of sodium 2-ethylhexanoate and 12 g of 2-ethylhexanoic acid. The solution is stirred for 4 hours at ambient room temperature, warmed to 40° C. and filtered. The ethanol is removed by heating in vacuo. The thick yellowish-green oil, 193 g, contains 15.89% Rh (97% yield).

Product yields of 21.6 and 14.4 weight-percent for Comparative Examples 1 and 2, respectively, are poor relative to yields ranging from 88 to 96.8 weight-percent obtained in Examples 1-3 of the present invention. The prior art procedure of the Comparative Examples also requires a number of additional steps, such as extraction and liquid-liquid separation, not required by the present invention.

The stability of the products prepared in accordance with this invention can be improved by incorporating various solubilizing and stabilizing agents such as, for example, ammonia, amines, chelating agents, amounts of at least one of the above-described organic carboxylic acids in excess of the amount required to neutralize the PGM and rhenium in the PGM and rhenium carboxylate, etc.

The organic solutions, and in particular the hydrocarbon solutions of the PGM salts of carboxylic acids, prepared in accordance with the present invention are useful as catalysts for hydrogenation reactions as is well known in the art. Examples of commercial processes which use organic solutions of PGM salts are the catalytic hydrogenation processes involving homogeneous catalysts described in Rylander, *Organic Syntheses with Noble Metal Catalysts* (Academic Press 1973) pp. 60–76, which is hereby incorporated herein by reference.

The PGM and rhenium salts of carboxylic acids prepared in accordance with the present invention can be recovered and isolated as crystalline solids, waxy solids, or oils depending on the specific carboxylate used. The techniques for recovering these products from the solutions of the present invention are well known in the art, such as by precipitation, evaporation, etc. Solid PGM salts can be decomposed under either oxidizing or reducing conditions to form PGM catalysts. For example, PGM carboxylates can be thermally decomposed at temperatures of about 250° C. or lower to form PGM catalysts. Generally, the decomposition temperature of the carboxylates of the present invention is less than about 180° C., and often less than about 150° C. Such low decomposition temperatures are advantageous for reducing the cost of making the catalyst and avoiding migration of PGM to the surface (known as "wicking"). The catalyst particles are characterized as having an enhanced surface area of metal per square unit area of metal and substrate, particularly when compared to, for example, the surface area of particles per square unit area of metal and substrate obtained by the oxidative or reductive decomposition of chloroplatinic acid at the same temperature.

The PGM and rhenium salts of the present invention which may be recovered from the solutions may be reduced under reducing conditions at elevated temperatures (generally below 240° C.) to form the desired PGM catalysts. For example, platinum neodecanoate isolated from a solution prepared in accordance with the present invention can be reduced to platinum metal at about 230° C. or less, and platinum 2-ethylhexanoate isolated from solutions prepared in accordance of the present invention can be decomposed in a reducing atmosphere to platinum at the temperature of about 165° C. or less. In contrast, chloroplatinic acid is reduced at a temperature of 400° C. or higher.

Supported catalysts also can be prepared in accordance with this invention by (1) depositing the PGM and rhenium salt solutions of the invention on supports such as alumina, (2) drying the treated support to remove the solvent, and optionally (3) decomposing the salt under either oxidizing or reducing conditions as described above to deposit the desired PGM and rhenium on the support. The metal or metal oxide catalyst prepared and isolated as described may be characterized as comprising small particle clusters which appear to be in the range from about 5 to about 20 Angstroms in diameter or less.

PGMs and rhenium have a variety of utilities as heterogeneous catalysts including utility in catalytic converters to treat exhaust emissions, chemical process catalysis and fuel cell catalytic electrodes. Platinum, palladium, and rhodium, for example, are useful in catalytic converters to treat automotive exhaust emissions and platinum-rhenium catalysts are useful in the production of unleaded gasoline and the production of benzene, toluene and xylenes by reforming.

The PGM and rhenium carboxylate salts, salt solutions, and the PGM and rhenium, and PGM and rhenium oxides, which can be prepared from the solutions prepared in accordance with the present invention also are characterized as being substantially free of chloride, nitrate and other anions. Because these anions have been known to reduce the effectiveness of these materials as catalysts, the absence of these anions is of substantial benefit to the practice of using these metals as catalysts.

The PGM and rhenium carboxylates made according to the present invention are also useful for preparing metallo-organic films. Metallo-organic films are useful for making electrical contacts, thin- and thick-film circuits and resistors; sensors; electrodes; solar energy collectors; reflective coatings, decorative coatings on china, glass and ceramics, etc. The metallo-organic film is generally decomposed to the metal(s) in these applications. Various PGM and/or rhenium carboxylates may be combined in the films to make alloys.

Micron-size PGM and rhenium features may, for example, be patterned by focusing the output of laser light energy, such as that emitted from a cw argon ion laser (514.5 nm) onto the PGM or rhenium organic film which has been filmed on a substrate. In one embodiment, micron-size platinum features are patterned by focusing the output of a cw argon ion laser onto a scanning quartz substrate coated with a spun-on platinum carboxylate film. The laser patterned deposition of platinum may then be used as a seed layer for electroless copper plating as described, for example, in Sausa et al, "Laser Decomposition of Platinum Metallo-Organic Films for Electroless Copper Plating," Journal of the Electrochemical Society, Volume 134, pp. 2707–2713, which is hereby fully incorporated herein by reference. The low level of laser energy required to decompose the platinum carboxylate of the metallo-organic film is advantageous for obtaining conductive patterns at high scan rates.

As mentioned above, another application for the platinum carboxylates prepared according to the present invention is to make oxygen sensors. In one embodiment, an oxygen sensor is prepared by coating an oxygen ion-conductive material with the platinum carboxylate prepared according to the present invention and heating the coated product to decompose the platinum carboxylate to platinum. The platinum metal coated surfaces conduct electrons in order to complete the circuit required for the migration of oxygen ions.

The ruthenium carboxylates prepared according to the present invention may be used to make a hydrogenation catalyst for hydrogenating unsaturated hydrocarbons. In one embodiment, ruthenium carboxylates prepared according to the present invention are coated on a substrate and heated to a temperature sufficient to decompose the carboxylate salt. The utility of these catalysts is more fully described in U.S. Pat. Nos.

3,562,181 and 3,748,332 and in the aforementioned Rylander, *Organic Syntheses with Noble Metal Catalysts,* ibid., pp. 60–67 and 74–76, which are hereby fully incorporated herein by reference.

The ruthenium carboxylates of the present invention may also be used to make ruthenium coated titanium-based electrodes used in caustic production. In one embodiment, titanium-based electrode coated with PGM oxides or double oxides formed by thermal decomposition may be used in the industrial electrolysis of salt water in which the platinum group oxides or double oxides may be selected from iridium oxide, rhodium oxide or ruthenium oxide prepared from the corresponding carboxylates made according to the present invention as described in, for example, Takahashi, "Electrochemical Studies on Improvement of Titanium-based Electrodes, etc.," Volume 39, pages 261–276, 439–454 and 531–540 (1988) and Volume 40, pages 313–330 (1989). In addition, ruthenium films provide chemical resistance in communication components and can be used as a diffusion barrier and adhesive layer, as a silicide former for low-ohmic contacts, and as a final metallization over platinum silicide for VLSI applications.

Thermocouple elements may also be made from platinum and rhodium carboxylates of the present invention and platinum-rhodium alloys prepared from mixed carboxylates are also useful in tools for glass manufacturing due to their resistance to corrosion and erosion by liquid glass.

As mentioned above, the PGM and rhenium carboxylates of the present invention can be produced substantially free of undesired cations such as chloride, nitrate and other anions. An added benefit of the absence of such anions can be the avoidance of undesired generation of corrosive compounds generated during or after decomposition of metallo-organo films produced from the carboxylates of the present invention. Examples of such corrosive compounds include hydrogen chloride gas, hydrochloric acid, nitrous oxides and nitric acid. The benefit of avoiding such corrosive compounds may be most noticeable when the metallo-organo films made from the carboxylates of the present invention are used in proximity to sensitive components such as electronic components and acid-sensitive substrates.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for preparing a platinum, palladium, osmium, iridium, rhodium or rhenium salt of a carboxylic acid comprising
   (A) preparing a mixture of
   (1) at least one alkali or alkaline earth metal salt of the carboxylic acid,
   (2) at least one platinum, palladium, osmium, iridium, rhodium or rhenium salt having an anion other than the carboxylate anion of (A)(1), and
   (3) an organic liquid capable of at least partly dissolving the at least one alkali or alkaline earth metal salt of the carboxylic acid (1) and the at least one platinum, palladium, osmium, iridium, rhodium or rhenium salt (2), which is not a solvent for a salt formed between the alkali or alkaline earth metal of (1) and the anion of (2); and
   (B) maintaining the mixture (A) at a temperature below the decomposition temperature of components (1), (2) and (3) and the platinum, palladium, osmium, iridium, rhodium or rhenium carboxylate product for a period of time sufficient to form the carboxylate product.

2. The method of claim 1 wherein the organic liquid comprises a ketone, a hydroxy-containing organic compound, an aromatic hydrocarbon, or a saturated ether, or a mixture thereof.

3. The method of claim 1 wherein the organic liquid comprises acetone, methyl ethyl ketone, ethanol, propanol, xylene or tetrahydrofuran, or a mixture thereof.

4. The method of claim 1 wherein at least 80 weight-percent of the carboxylic acid of (A)(1) is at least one aliphatic carboxylic acid having from 4 to about 30 carbon atoms.

5. The method of claim 1 wherein the alkali or alkaline earth metal salt of the carboxylic acid of (A)(1) comprises an alkali or alkaline earth metal salt of propionic acid, butyric acid, isopentanoic acid, 2-ethylbutyric acid, nonanoic acid, decanoic acid, 2-ethylhexanoic acid, isooctanoic acid, isononanoic acid, neodecanoic acid, dodecanoic acid, lauric acid, palmitic acid, stearic acid, oleic acid, linoleic acid, naphthenic acids, tall oil acids, or rosin acids, or a mixture thereof.

6. The method of claim 1 wherein the metal of said alkali or alkaline earth metal salt of the carboxylic acid of (A)(1) is an alkali metal.

7. The method of claim 6 wherein the alkali metal comprises sodium or potassium.

8. The method of claim 1 wherein the salt of (A)(2) comprises a platinum salt.

9. The method of claim 8 wherein the platinum salt comprises platinum tetrachloride, platinum trichloride, or platinum dichloride, or a mixture of two or more of these chlorides.

10. The method of claim 8 wherein the platinum salt comprises platinum tetrachloride.

11. The method of claim 1 wherein the salt of (A)(2) comprises a palladium salt.

12. The method of claim 1 wherein the salt of (A)(2) comprises an osmium salt.

13. The method of claim 1 wherein the salt of (A)(2) comprises a rhodium salt.

14. The method of claim 1 wherein the salt of (A)(2) comprises an iridium salt.

15. The method of claim 1 wherein the salt of (A)(2) comprises a rhenium salt.

16. The method of claim 1 conducted at a temperature in the range from about 20° C. to about 100° C.

17. The method of claim 1 further comprising
   (C) filtering the product produced in (B) and recovering the filtrate.

18. The method of claim 17 further comprising
   (D) evaporating the organic liquid of (A)(3) from the filtrate to form a filtrate residue; and
   (E) treating the filtrate residue with a second organic liquid different from the organic liquid of (A)(3).

19. The method of claim 18 further comprising
   (F) filtering the second organic liquid containing the dissolved filtrate residue.

20. The method of claim 19 wherein the filtrate contains at least 80 weight-percent carboxylate product (B) yield.

13

21. The method of claim 19 wherein the filtrate contains at least 90 weight-percent carboxylate product (B) yield.

22. The method of claim 20 wherein at least about 80 weight-percent of the carboxylic acid of (A)(1) is at least one carboxylic acid having from 6 to about 30 carbon atoms.

23. The method of claim 1 wherein the molar ratio of the alkali or alkaline earth metal of the carboxylic acid (1) to the salt (2) in (A) is in the range from about 1:1 to about 10:1.

24. A method of preparing a platinum salt of a carboxylic acid consisting essentially of the steps of:
(A) preparing a mixture of
(1) at least one alkali or alkaline earth metal salt of the carboxylic acid having from about 6 to about 30 carbon atoms,
(2) at least one platinum chloride, and
(3) an organic liquid capable of at least partially dissolving the at least one alkali or alkaline earth metal salt of the carboxylic acid (1) and the at least one platinum chloride (2), which is not a solvent for a salt formed between the alkali or alkaline earth metal of (1) and the chloride of (2); and
(B) maintaining the mixture of (A) at a temperature in the range from about 20° C. to about 150° C. for a period of time sufficient to form the platinum carboxylate.

25. The method of claim 24 wherein the organic liquid comprises a ketone.

26. The method of claim 24 wherein the platinum chloride comprises $PtCl_4$ and the organic liquid comprises acetone.

27. The method of claim 24 wherein the temperature of the mixture (B) is maintained in the range from about 45° C. to about 80° C.

28. The method of claim 24 further comprising:
(C) filtering the product of (B) and recovering the filtrate;
(D) evaporating the organic liquid of (A)(3) from the filtrate to form a filtrate residue; and
(E) treating the filtrate residue with a second organic liquid different from the organic liquid of (A)(3) to dissolve the desired platinum carboxylate.

29. The method of claim 28 wherein the organic liquid of (A)(3) comprises a ketone and the second organic liquid of (D) comprises a hydroxy-containing organic compound.

30. The method of claim 28 wherein the organic liquid of (A)(3) is acetone and the second organic liquid of (D) is xylene.

31. The method of claim 24 wherein the alkali or alkaline earth metal of (A)(1) comprises sodium or potassium.

32. The method of claim 24 wherein the alkali or alkaline earth metal salt of the carboxylic acid of (A)(1) comprises an alkali or alkaline earth metal salt of hexanoic acid, 2-ethylbutyric acid, nonanoic acid, decanoic acid, 2-ethylhexanoic acid, isooctanoic acid, isononanoic acid, neodecanoic acid, dodecanoic acid, lauric acid, palmitic acid, stearic acid, oleic acid, linoleic acid, naphthenic acids, tall oil acids, or rosin acids, or a mixture thereof.

33. The method of claim 24 wherein the alkali or alkaline earth metal salt of the carboxylic acid of (A)(1) comprises an alkali or alkaline earth metal salt of neodecanoic acid.

14

34. The method of claim 1 wherein the organic liquid comprises acetone, methyl ethyl ketone, propanol, xylene or tetrahydrofuran, or a mixture thereof.

35. The method of claim 1 wherein the organic liquid does not comprise ethanol.

36. The method of claim 18 wherein the organic liquid of (A)(3) comprises a ketone and the second organic liquid of (D) comprises an aromatic solvent.

37. The method of claim 18 wherein the organic liquid of (A)(3) comprises acetone and the second organic liquid of (D) comprises xylene.

38. A method for preparing a platinum group metal or rhenium salt of a carboxylic acid comprising
(A) preparing a mixture of
(1) at least one alkali or alkaline earth metal salt of the carboxylic acid,
(2) at least one platinum group metal or rhenium salt having an anion other than the carboxylate anion of (A)(1), and
(3) an organic liquid capable of at least partly dissolving the at least one alkali or alkaline earth metal salt of the carboxylic acid (1) and the at least one platinum group metal or rhenium salt (2), which is not a solvent for a salt formed between the alkali or alkaline earth metal of (1) and the anion of (2); and
(B) maintaining the mixture (A) at a temperature below the decomposition temperature of components (1), (2) and (3) and platinum group metal or rhenium carboxylate product for a period of time sufficient to form the platinum group metal or rhenium carboxylate product,
wherein at least 80 weight-percent of the carboxylic acid of (A)(1) is at least one aliphatic carboxylic acid having from 4 to about 30 carbon atoms.

39. The method of claim 38 wherein the organic liquid comprises a ketone, a hydroxy-containing organic compound, an aromatic hydrocarbon, or a saturated ether, or a mixture thereof.

40. The method of claim 38 wherein the organic liquid comprises acetone, methyl ethyl ketone, ethanol, propanol, xylene or tetrahydrofuran, or a mixture thereof.

41. The method of claim 38 wherein the organic liquid comprises acetone, methyl ethyl ketone, xylene or tetrahydrofuran, or a mixture thereof.

42. The method of claim 38 wherein said salt of (A)(2) comprises a platinum salt.

43. The method of claim 38 wherein said salt of (A)(2) comprises a palladium salt.

44. The method of claim 38 wherein the salt of (A)(2) comprises an osmium salt.

45. The method of claim 38 wherein the salt of (A)(2) comprises a rhodium salt.

46. The method of claim 38 wherein the salt of (A)(2) comprises an iridium salt.

47. The method of claim 38 wherein the salt of (A)(2) comprises a rhenium salt.

48. The method of claim 38 wherein the salt of (A)(2) comprises a ruthenium salt.

49. The method of claim 38 further comprising
(C) filtering the product produced in (B) and recovering the filtrate;
(D) evaporating the organic liquid of (A)(3) from the filtrate to form a filtrate residue;
(E) treating the filtrate residue with a second organic liquid different from the organic liquid of (A)(3); and (F) filtering the second organic liquid containing the dissolved filtrate residue.

50. The method of claim 49 wherein the organic liquid of (A)(3) comprises a ketone and the second organic liquid of (D) comprises an aromatic solvent.

51. A method for preparing a platinum group metal or rhenium salt of a carboxylic acid comprising
   (A) preparing a mixture of
      (1) at least one alkali or alkaline earth metal salt of the carboxylic acid,
      (2) at least one platinum group metal or rhenium salt having an anion other than the carboxylate anion of (A)(1), and
      (3) a first organic liquid capable of at least partly dissolving the at least one alkali or alkaline earth metal salt of the carboxylic acid (1) and the at least one platinum group metal or rhenium salt (2), which is not a solvent for a salt formed between the alkali or alkaline earth metal of (1) and the anion of (2); and
   (B) maintaining the mixture (A) at a temperature below the decomposition temperature of components (1), (2) and (3) and platinum group metal or rhenium carboxylate product for a period of time sufficient to form the platinum group metal or rhenium carboxylate product,
   wherein the first organic liquid comprises a ketone, an aromatic hydrocarbon, or a saturated ether, or a mixture thereof.

52. The method of claim 51 wherein the first organic liquid comprises acetone, methyl ethyl ketone, xylene or tetrahydrofuran, or a mixture thereof.

53. The method of claim 51 wherein said platinum group metal or rhenium salt comprises a platinum salt.

54. The method of claim 51 wherein said platinum group metal or rhenium salt comprises a palladium salt.

55. The method of claim 51 wherein the platinum group metal or rhenium salt comprises a ruthenium salt.

56. The method of claim 51 wherein the platinum group metal or rhenium salt comprises a rhenium salt.

57. The method of claim 51 wherein the method further comprises:
   (C) filtering the product produced in (B) and recovering the filtrate;
   (D) evaporating the organic liquid of (A)(3) from the filtrate to form a filtrate residue; and
   (E) treating the filtrate residue with a second organic liquid different from the organic liquid of (A)(3), wherein the first organic liquid of (A)(3) comprises a ketone and the second organic liquid of (E) comprises an aromatic hydrocarbon.

58. The method of claim 57 wherein the first organic liquid of (A)(3) comprises acetone or methyl ethyl ketone and the second organic liquid of (E) comprises xylene.

59. The method of claim 57 wherein said platinum group metal or rhenium salt comprises a platinum salt.

60. The method of claim 57 wherein said platinum group metal or rhenium salt comprises a palladium salt.

61. The method of claim 57 wherein the platinum group metal or rhenium salt comprises a rhenium salt.

62. The method of claim 17 further comprising
   (C1) rinsing the reaction vessel, precipitates, and filter medium with a platinum group metal or rhenium carboxylate solvent more volatile than the organic liquid into the filtrate solution and
   (C2) removing the solvent from the filtrate solution using heat, reduced pressure, or both.

63. A method for preparing a platinum group metal or rhenium salt of a carboxylic acid comprising
   (A) preparing a mixture of
      (1) at least one alkali or alkaline earth metal salt of the carboxylic acid,
      (2) at least one platinum group metal or rhenium salt having an anion other than the carboxylate anion of (A)(1), and
      (3) an organic liquid capable of at least partly dissolving the at least one alkali or alkaline earth metal salt of the carboxylic acid (1) and the at least one platinum group metal or rhenium salt (2), which is not a solvent for a salt formed between the alkali or alkaline earth metal of (1) and the anion of (2) and
   (B) maintaining the mixture (A) at a temperature in the range from about 20° C. to about 100° C. for a period of time sufficient to form the platinum group metal or rhenium carboxylate.

64. The process of claim 63 wherein the temperature of (B) does not exceed about 80° C.

65. The process of claim 64 wherein the organic liquid of (A)(3) is a hydroxy-containing compound.

66. The method of claim 65 wherein the at least one platinum group metal or rhenium salt of (A)(2) comprises a rhodium or ruthenium salt.

67. The method of claim 66 wherein the salt of (A)(2) is a ruthenium salt and the organic liquid of (A)(3) comprises ethanol.

* * * * *